(12) United States Patent
Angel (10) Patent No.: US 8,777,981 B2
(45) Date of Patent: *Jul. 15, 2014

(54) MULTI-LUMEN CENTRAL ACCESS VENA CAVA FILTER APPARATUS AND METHOD OF USING SAME

(75) Inventor: Luis F. Angel, San Antonio, TX (US)

(73) Assignee: Bio2Medical, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/598,358

(22) Filed: Aug. 29, 2012

(65) Prior Publication Data

US 2013/0060275 A1 Mar. 7, 2013

Related U.S. Application Data

(63) Continuation of application No. 11/849,225, filed on Aug. 31, 2007, now Pat. No. 8,668,712.

(51) Int. Cl.
*A61M 29/00* (2006.01)

(52) U.S. Cl.
USPC .......... 606/200; 623/1.11; 604/104; 604/106; 604/107

(58) Field of Classification Search
USPC ........... 606/200; 604/104, 106, 107; 623/1.11
See application file for complete search history.

(56) References Cited

U.S. PATENT DOCUMENTS

| | | | |
|---|---|---|---|
| 3,671,979 A | 6/1972 | Moulopoulos | 3/1 |
| 4,901,731 A | 2/1990 | Millar | 128/675 |
| 4,921,479 A | 5/1990 | Grayzel | 604/53 |
| 4,969,891 A | 11/1990 | Gewertz | 606/200 |
| 5,046,503 A | 9/1991 | Schneiderman | 128/692 |
| 5,053,008 A | 10/1991 | Bajaj | 604/104 |
| 5,112,347 A | 5/1992 | Taheri | 606/200 |
| 5,163,928 A | 11/1992 | Hobbs et al. | 604/281 |
| 5,201,757 A | 4/1993 | Heyn et al. | 606/200 |
| 5,549,626 A | 8/1996 | Miller et al. | 606/200 |
| 5,569,215 A | 10/1996 | Crocker | 604/264 |
| 5,624,396 A | 4/1997 | McNamara et al. | 604/93 |
| 5,707,389 A | 1/1998 | Louw et al. | 606/200 |

(Continued)

FOREIGN PATENT DOCUMENTS

| WO | 96/30073 | 10/1996 | A61M 29/00 |
|---|---|---|---|
| WO | 97/17100 | 5/1997 | A61M 29/00 |

(Continued)

OTHER PUBLICATIONS

Decousus, Herve, et al., "A Clinical Trial of Vena Caval Filters in the Prevention of Pulmonary Embolism in Patients with Proximal Deep-Vein Thrombisis", *The New England Journal of Medicine*, vol. 338, No. 7, pp. 409-415 (Feb. 12, 1998).

(Continued)

*Primary Examiner* — Victor Nguyen
*Assistant Examiner* — Kevin Everage
(74) *Attorney, Agent, or Firm* — David G. Rosenbaum; J. Peter Paredes; Rosenbaum IP (57) ABSTRACT

A combined multi-lumen central access catheter and an embolic filter including ports proximal and distal the filter for fluid infusion and/or pressure sensing and infusion ports in the catheter to permit infusion of bioactive agents, flushing agents and/or contrast agents. The embolic filter may be removably coupled to the multi-lumen catheter for temporary placement and retrieval under recommended indications.

26 Claims, 9 Drawing Sheets

(56) References Cited

U.S. PATENT DOCUMENTS

| | | | |
|---|---|---|---|
| 5,715,829 A | 2/1998 | Arand et al. | 128/673 |
| 5,766,151 A | 6/1998 | Valley et al. | 604/96 |
| 5,769,816 A | 6/1998 | Barbut et al. | 604/96 |
| 5,791,341 A | 8/1998 | Bullard | 128/207.15 |
| 5,795,322 A | 8/1998 | Boudewijn | 604/22 |
| 5,795,325 A | 8/1998 | Valley et al. | 604/53 |
| 5,797,920 A | 8/1998 | Kim | 606/108 |
| 5,814,064 A | 9/1998 | Daniel et al. | 606/200 |
| 5,833,650 A | 11/1998 | Imran | 604/53 |
| 5,848,964 A | 12/1998 | Samuels | 600/200 |
| 5,879,499 A | 3/1999 | Corvi | 156/175 |
| 5,893,868 A | 4/1999 | Hanson et al. | 606/198 |
| 5,925,016 A | 7/1999 | Chornenky et al. | 604/96 |
| 5,947,994 A | 9/1999 | Louw et al. | 606/200 |
| 5,947,995 A | 9/1999 | Samuels | 606/200 |
| 5,954,742 A | 9/1999 | Osypka | 606/198 |
| 5,976,172 A | 11/1999 | Homsma et al. | 606/200 |
| 5,980,478 A | 11/1999 | Gorsuch et al. | 604/4 |
| 5,980,555 A | 11/1999 | Barbut et al. | 600/200 |
| 5,989,281 A | 11/1999 | Barbut et al. | 606/200 |
| 6,007,544 A | 12/1999 | Kim | 606/108 |
| 6,036,654 A | 3/2000 | Quinn et al. | 600/526 |
| 6,051,014 A | 4/2000 | Jang | 606/200 |
| 6,086,605 A | 7/2000 | Barbut et al. | 606/200 |
| 6,090,097 A | 7/2000 | Barbut et al. | 604/511 |
| 6,117,154 A | 9/2000 | Barbut et al. | 606/181 |
| 6,135,991 A | 10/2000 | Muni et al. | 604/509 |
| 6,136,016 A | 10/2000 | Barbut et al. | 606/200 |
| 6,152,909 A | 11/2000 | Bagaoisan et al. | 604/523 |
| 6,165,179 A | 12/2000 | Cathcart et al. | 606/108 |
| 6,171,328 B1 | 1/2001 | Addis | 606/200 |
| 6,178,968 B1 | 1/2001 | Louw et al. | 128/898 |
| 6,179,813 B1 | 1/2001 | Ballow et al. | 604/164 |
| 6,224,627 B1 | 5/2001 | Armstrong et al. | 623/1.23 |
| 6,231,544 B1 | 5/2001 | Tsugita et al. | 604/104 |
| 6,235,045 B1 | 5/2001 | Barbut et al. | 606/200 |
| 6,251,093 B1 | 6/2001 | Valley et al. | 604/96 |
| 6,270,477 B1 | 8/2001 | Bagaoisan et al. | 604/96.01 |
| 6,277,138 B1 | 8/2001 | Levinson et al. | 606/200 |
| 6,287,321 B1 | 9/2001 | Jang | 606/200 |
| 6,315,792 B1 | 11/2001 | Armstrong et al. | 623/1.13 |
| 6,336,934 B1 | 1/2002 | Gilson et al. | 606/200 |
| 6,344,049 B1 | 2/2002 | Levinson et al. | 606/200 |
| 6,344,053 B1 | 2/2002 | Boneau | 623/1.11 |
| 6,379,373 B1 | 4/2002 | Sawhney et al. | 606/193 |
| 6,383,196 B1 | 5/2002 | Leslie et al. | 606/114 |
| 6,423,086 B1 | 7/2002 | Barbut et al. | 606/200 |
| 6,432,122 B1 | 8/2002 | Gilson et al. | 606/200 |
| 6,443,971 B1 | 9/2002 | Boylan et al. | 606/200 |
| 6,454,741 B1 | 9/2002 | Muni et al. | 604/96.01 |
| 6,468,291 B2 * | 10/2002 | Bates et al. | 606/200 |
| 6,482,171 B1 | 11/2002 | Corvi et al. | 604/96.01 |
| 6,511,503 B1 | 1/2003 | Burkett et al. | 623/1.11 |
| 6,537,294 B1 | 3/2003 | Boyle et al. | 606/200 |
| 6,537,296 B2 * | 3/2003 | Levinson et al. | 606/200 |
| 6,544,279 B1 | 4/2003 | Hopkins et al. | 606/200 |
| 6,547,788 B1 | 4/2003 | Maguire et al. | 604/41 |
| 6,561,996 B1 | 5/2003 | Gorsuch | 604/6.09 |
| 6,569,148 B2 | 5/2003 | Bagaoisan et al. | 604/509 |
| 6,585,639 B1 | 7/2003 | Kotmel et al. | 600/116 |
| 6,589,264 B1 | 7/2003 | Barbut et al. | 606/200 |
| 6,592,546 B1 | 7/2003 | Barbut et al. | 604/96.01 |
| 6,596,011 B2 | 7/2003 | Johnson et al. | 606/200 |
| 6,616,680 B1 | 9/2003 | Thielen | 606/200 |
| 6,623,507 B2 | 9/2003 | Saleh | 606/200 |
| 6,635,070 B2 | 10/2003 | Leeflang et al. | 606/200 |
| 6,669,708 B1 | 12/2003 | Nissenbaum et al. | 606/153 |
| 6,685,722 B2 | 2/2004 | Rosenbluth et al. | 606/200 |
| 6,689,148 B2 | 2/2004 | Sawhney et al. | 606/193 |
| 6,692,512 B2 | 2/2004 | Jang | 606/200 |
| 6,726,651 B1 | 4/2004 | Robinson et al. | 604/101.01 |
| 6,726,702 B2 | 4/2004 | Khosravi | 606/200 |
| 6,749,619 B2 | 6/2004 | Ouriel et al. | 606/200 |
| 6,755,813 B2 * | 6/2004 | Ouriel et al. | 604/537 |
| 6,780,193 B2 | 8/2004 | Leslie et al. | 606/114 |
| 6,805,692 B2 | 10/2004 | Muni et al. | 604/509 |
| 6,869,431 B2 | 3/2005 | Maguire et al. | 604/41 |
| 6,885,115 B2 | 4/2005 | Hatori et al. | 307/80 |
| 6,887,257 B2 | 5/2005 | Salahieh et al. | 606/200 |
| 6,913,600 B2 | 7/2005 | Valley et al. | 604/509 |
| 6,986,778 B2 | 1/2006 | Zadno-Azizi | 606/200 |
| 6,997,938 B2 | 2/2006 | Wang et al. | 606/200 |
| 7,011,672 B2 | 3/2006 | Barbut et al. | 606/200 |
| 7,060,082 B2 | 6/2006 | Goll et al. | 606/200 |
| 7,108,708 B2 | 9/2006 | Cheng et al. | 606/200 |
| 7,125,414 B2 | 10/2006 | Blackledge et al. | 606/200 |
| 7,144,408 B2 | 12/2006 | Keegan et al. | 606/200 |
| 7,150,737 B2 | 12/2006 | Purdy et al. | 604/506 |
| 7,153,320 B2 | 12/2006 | Euteneuer et al. | 606/200 |
| 7,163,520 B2 | 1/2007 | Bernard et al. | 604/6.9 |
| 7,166,570 B2 | 1/2007 | Hunter et al. | 514/2 |
| 7,220,270 B2 | 5/2007 | Sawhney et al. | 606/193 |
| 7,261,727 B2 | 8/2007 | Thielen | 606/200 |
| 7,399,308 B2 | 7/2008 | Borillo et al. | 606/200 |
| 2001/0001812 A1 | 5/2001 | Valley et al. | 604/96.01 |
| 2001/0031981 A1 | 10/2001 | Evans et al. | 606/200 |
| 2001/0044634 A1 | 11/2001 | Don Michael et al. | 606/200 |
| 2002/0062134 A1 | 5/2002 | Barbut et al. | 606/200 |
| 2002/0072730 A1 | 6/2002 | McGill et al. | 604/525 |
| 2002/0082525 A1 | 6/2002 | Oslund et al. | 600/585 |
| 2002/0082636 A1 | 6/2002 | Sawhney et al. | 606/193 |
| 2002/0091407 A1 | 7/2002 | Zadno-Azizi et al. | 606/200 |
| 2002/0107479 A1 | 8/2002 | Bates et al. | 604/96.01 |
| 2002/0107506 A1 | 8/2002 | McGuckin, Jr. et al. | 604/523 |
| 2002/0165575 A1 | 11/2002 | Saleh | 606/200 |
| 2002/0188313 A1 | 12/2002 | Johnson et al. | 606/200 |
| 2003/0009146 A1 | 1/2003 | Muni et al. | 604/500 |
| 2003/0032941 A1 | 2/2003 | Boyle et al. | 604/533 |
| 2003/0050600 A1 | 3/2003 | Ressemann et al. | 604/101.01 |
| 2003/0093110 A1 | 5/2003 | Vale | 606/200 |
| 2003/0097082 A1 | 5/2003 | Purdy et al. | 606/594 |
| 2003/0097094 A1 | 5/2003 | Ouriel et al. | 604/93.01 |
| 2003/0125764 A1 | 7/2003 | Brady et al. | 606/200 |
| 2003/0176889 A1 | 9/2003 | Boyle et al. | 606/200 |
| 2003/0187495 A1 | 10/2003 | Cully et al. | 623/1.15 |
| 2003/0203031 A1 | 10/2003 | Shah | 424/485 |
| 2003/0208222 A1 | 11/2003 | Zadno-Azizi | 606/194 |
| 2003/0212434 A1 | 11/2003 | Thielen | 606/200 |
| 2003/0233117 A1 | 12/2003 | Adams et al. | 606/200 |
| 2004/0006367 A1 | 1/2004 | Johnson et al. | 606/200 |
| 2004/0006368 A1 | 1/2004 | Mazzocchi et al. | 606/200 |
| 2004/0011740 A1 | 1/2004 | Bernard et al. | 210/646 |
| 2004/0044302 A1 | 3/2004 | Bernard et al. | 604/6.09 |
| 2004/0102806 A1 * | 5/2004 | Broome et al. | 606/200 |
| 2004/0153112 A1 | 8/2004 | Nissenbaum et al. | 606/185 |
| 2004/0158276 A1 | 8/2004 | Barbut et al. | 606/200 |
| 2004/0162576 A1 | 8/2004 | Barbut et al. | 606/200 |
| 2004/0199177 A1 | 10/2004 | Kim | 606/108 |
| 2004/0220612 A1 | 11/2004 | Swainston et al. | 606/200 |
| 2004/0236170 A1 | 11/2004 | Kim | 600/16 |
| 2004/0254528 A1 | 12/2004 | Adams et al. | 604/96.01 |
| 2005/0021075 A1 | 1/2005 | Bonnette et al. | 606/200 |
| 2005/0027236 A1 | 2/2005 | Douk | 604/40 |
| 2005/0038503 A1 | 2/2005 | Greenhalgh et al. | 623/1.42 |
| 2005/0080445 A1 | 4/2005 | Sawhney et al. | 606/193 |
| 2005/0085769 A1 | 4/2005 | MacMahon et al. | 604/96.01 |
| 2005/0085841 A1 | 4/2005 | Eversull et al. | 606/190 |
| 2005/0107817 A1 | 5/2005 | White et al. | 606/191 |
| 2005/0113862 A1 | 5/2005 | Besselink et al. | 606/200 |
| 2005/0133046 A1 | 6/2005 | Becker et al. | 128/898 |
| 2005/0142163 A1 | 6/2005 | Hunter et al. | 424/423 |
| 2005/0145258 A1 | 7/2005 | Dong | 128/898 |
| 2005/0147562 A1 | 7/2005 | Hunter et al. | 424/9.5 |
| 2005/0147599 A1 | 7/2005 | Hunter et al. | 424/94.63 |
| 2005/0147643 A1 | 7/2005 | Hunter et al. | 424/423 |
| 2005/0148512 A1 | 7/2005 | Hunter et al. | 514/12 |
| 2005/0148997 A1 | 7/2005 | Valley et al. | 604/509 |
| 2005/0158274 A1 | 7/2005 | Hunter et al. | 424/78.38 |
| 2005/0169958 A1 | 8/2005 | Hunter et al. | 424/423 |
| 2005/0169959 A1 | 8/2005 | Hunter et al. | 424/423 |
| 2005/0175657 A1 | 8/2005 | Hunter et al. | 424/422 |
| 2005/0177186 A1 | 8/2005 | Cully et al. | 606/200 |
| 2005/0186247 A1 | 8/2005 | Hunter et al. | 424/423 |
| 2005/0191248 A1 | 9/2005 | Hunter et al. | 424/50 |

(56) References Cited

U.S. PATENT DOCUMENTS

| | | | |
|---|---|---|---|
| 2005/0192620 A1 | 9/2005 | Cully et al. | 606/200 |
| 2005/0197624 A1 | 9/2005 | Goodson, IV et al. | 604/96.01 |
| 2005/0205097 A1 | 9/2005 | Kyle, Jr. | 128/207.14 |
| 2005/0245962 A1 | 11/2005 | Adams et al. | 606/194 |
| 2005/0261733 A1 | 11/2005 | Cheng et al. | 606/200 |
| 2005/0267408 A1 | 12/2005 | Grandt et al. | 604/103.04 |
| 2005/0267442 A1 | 12/2005 | Von Oepen | 604/509 |
| 2005/0277976 A1 | 12/2005 | Galdonik et al. | 606/200 |
| 2005/0283182 A1 | 12/2005 | Pierce et al. | 606/200 |
| 2006/0047300 A1 | 3/2006 | Eidenschink | |
| 2006/0135961 A1 | 6/2006 | Rosenman et al. | 606/108 |
| 2006/0189921 A1 | 8/2006 | Galdonik et al. | 604/27 |
| 2006/0190025 A1 | 8/2006 | Lehe et al. | 606/200 |
| 2006/0200191 A1 | 9/2006 | Zadno-Azizi | 606/200 |
| 2006/0229657 A1 | 10/2006 | Wasicek et al. | 606/200 |
| 2006/0240063 A9 | 10/2006 | Hunter et al. | 424/423 |
| 2006/0240064 A9 | 10/2006 | Hunter et al. | 424/423 |
| 2006/0241675 A1 | 10/2006 | Johnson et al. | 606/200 |
| 2006/0241676 A1 | 10/2006 | Johnson et al. | 606/200 |
| 2006/0241677 A1 | 10/2006 | Johnson et al. | 606/200 |
| 2006/0241678 A1 | 10/2006 | Johnson et al. | 606/200 |
| 2006/0241679 A1 | 10/2006 | Johnson et al. | 606/200 |
| 2006/0241680 A1 | 10/2006 | Johnson et al. | 606/200 |
| 2006/0248871 A1 | 11/2006 | Johnson et al. | 57/58.83 |
| 2006/0271098 A1 | 11/2006 | Peacock, III | 606/200 |
| 2007/0006441 A1 | 1/2007 | McNiven et al. | 29/508 |
| 2007/0016132 A1 | 1/2007 | Oepen et al. | 604/96.01 |
| 2007/0016165 A1 | 1/2007 | Von Oepen et al. | 604/525 |
| 2007/0021771 A1 | 1/2007 | Oepen et al. | 606/194 |
| 2007/0055365 A1 | 3/2007 | Greenberg et al. | 623/1.44 |
| 2007/0060942 A2 | 3/2007 | Zadno-Azizi | 606/194 |
| 2007/0065484 A1 | 3/2007 | Chudzik et al. | 424/426 |
| 2007/0083188 A1 | 4/2007 | Grandt et al. | 604/524 |
| 2007/0123838 A1 | 5/2007 | Bernard et al. | 604/500 |
| 2007/0129752 A1* | 6/2007 | Webler et al. | 606/200 |
| 2007/0129753 A1 | 6/2007 | Quinn et al. | 606/200 |
| 2007/0191717 A1 | 8/2007 | Rosen et al. | 600/485 |
| 2007/0204455 A1 | 9/2007 | Knott et al. | 29/508 |
| 2007/0244503 A1 | 10/2007 | Casey et al. | 606/200 |
| 2007/0293930 A1 | 12/2007 | Wang et al. | 623/1.11 |
| 2008/0027481 A1 | 1/2008 | Gilson et al. | 606/200 |
| 2008/0051671 A1 | 2/2008 | Broome et al. | 600/504 |
| 2008/0262532 A1 | 10/2008 | Martin | |
| 2009/0043332 A1* | 2/2009 | Sullivan et al. | 606/200 |

FOREIGN PATENT DOCUMENTS

| | | | |
|---|---|---|---|
| WO | 97/42879 | 11/1997 | A61B 17/00 |
| WO | 98/46297 | 10/1998 | A61M 29/00 |
| WO | 99/65420 | 12/1999 | A61F 2/06 |
| WO | 00/09190 | 2/2000 | A61M 25/00 |
| WO | 01/13983 | 3/2001 | A61M 25/00 |
| WO | 01/37921 | 5/2001 | A61M 29/00 |
| WO | 01/65936 | 9/2001 | C12N 11/04 |
| WO | 02/30271 | 4/2002 | |
| WO | 02/39878 | 5/2002 | |
| WO | 02/40090 | 5/2002 | A61M 29/00 |
| WO | 03/015859 | 2/2003 | A61M 25/06 |
| WO | 03/084437 | 10/2003 | A61F 2/03 |
| WO | 2004/014240 | 2/2004 | A61B 17/12 |
| WO | 2004/034884 | 4/2004 | |
| WO | 2004/054650 | 7/2004 | A61M 25/00 |
| WO | 2004/060465 | 7/2004 | A61M 25/06 |
| WO | 2004/098674 | 11/2004 | |
| WO | 2005/011786 | 2/2005 | A61M 25/00 |
| WO | 2005/023358 | 3/2005 | A61M 25/00 |
| WO | 2005/046746 | 5/2005 | A61B 17/11 |
| WO | 2005/058384 | 6/2005 | A61L 29/00 |
| WO | 2005/065079 | 7/2005 | A61F 2/02 |
| WO | 2005/074520 | 8/2005 | |
| WO | 2005/091910 | 10/2005 | |
| WO | 2005/118044 | 12/2005 | A61M 25/00 |
| WO | 2005/118045 | 12/2005 | A61M 25/00 |
| WO | 2005/118050 | 12/2005 | A61M 29/00 |
| WO | 2006/065949 | 6/2006 | A61F 11/10 |
| WO | 2006/074163 | 7/2006 | B01D 71/06 |
| WO | 2006/089178 | 8/2006 | A61M 25/00 |
| WO | 2006/104591 | 10/2006 | A61M 25/00 |
| WO | 2006/105065 | 10/2006 | A61F 2/01 |
| WO | 2006/116636 | 11/2006 | A61F 2/06 |
| WO | 2006/127929 | 11/2006 | A61M 29/00 |
| WO | 2007/035865 | 3/2007 | A61M 27/00 |
| WO | 2007/035885 | 3/2007 | A61L 21/20 |
| WO | 2008/010197 | 1/2008 | A61F 2/01 |

OTHER PUBLICATIONS

Lin, Peter H., et al., "Vena Caval Filters in the Treatment of Acute DVT", *Endovascular Today*, pp. 40-50 (Jan. 2005).
Examination Report issued in corresponding foreign application, European Patent Application No. 08799012.3, pp. 1-4 (Sep. 9, 2013).

* cited by examiner

MULTI-LUMEN CENTRAL ACCESS VENA CAVA FILTER APPARATUS AND METHOD OF USING SAME

CROSS-REFERENCE TO RELATED APPLICATIONS

The present invention is a continuation of U.S. patent application Ser. No. 11/849,225, filed Aug. 31, 2007, and incorporated by reference herein.

BACKGROUND OF THE INVENTION

The present invention pertains generally to the field of vascular filters for capturing embolic material in the blood flow.

The accepted standard of care for patients with venous thromboembolism (VTE) is anticoagulant therapy. Inferior vena cava (IVC) filters are reserved for those patients who fail anticoagulant therapy, or have a complication or contraindication to anticoagulant therapy. Until the early 1970's, the only method of IVC interruption was surgical, either by clipping, ligation or plication. The first clinical experience of an endoluminally-placed device to interrupt IVC flow was reported by Mobin-Uddin et al. in 1969. However, it was not until the introduction of a stainless steel umbrella-type filter by Greenfield et al. in 1973 that an effective method of endoluminally trapping emboli while simultaneously preserving IVC flow became possible. Indeed, for many years, the Greenfield filter set a benchmark by which newer filters were measured. Early generations of filters were inserted by surgical cut-down and venotomy. Eventually filters were able to be inserted percutaneously: initially through large 24 Fr sheaths, though newer generations of filters are able to be delivered through 6 Fr systems.

Despite the safety and efficacy of modern day filters, systemic anticoagulation remains the primary treatment for VTE. Either unfractionated or low molecular weight heparin followed by three months of oral anticoagulation in patients with proximal deep venous thrombosis (DVT) is approximately 94% effective in preventing pulmonary embolism (PE) or recurrent DVT. The routine placement of IVC filters in addition to anticoagulation in patients with documented DVT was investigated by Decousus et al. in a randomized trial. Decousus H, Leizorovicz A, Parent F, et al. A clinical trial of vena caval filters in the prevention of pulmonary embolism in patients with proximal deep-vein thrombosis. *N Engl J Med* 1998;338:409-415. This study revealed that the use of a permanent filter in addition to heparin therapy significantly decreased the occurrence of PE within the first 12 days compared to those without a filter. However, no effect was observed on either immediate or long-term mortality, and by 2 years, the initial benefit seen in the group of patients with filters was offset by a significant increase in the rate of recurrent DVT.

Despite the efficacy of anticoagulant therapy in the management of VTE, there are certain situations and conditions in which the benefits of anticoagulation are outweighed by the risks of instituting such a therapy. These include contraindications and complications of anticoagulant therapy. In such circumstances, there may be absolute or relative indications for filter insertion Currently, there are eight different types of permanent cava filters that are FDA approved. These include the Bird's Nest filter (Cook Incorporated, Bloomington, Ind.), Vena Tech LGM filter (B. Braun, Bethlehem Pa.), Vena Tech LP (B. Braun), Simon Nitinol filter (Bard, Covington, Ga.), Titanium Greenfield filter (Boston Scientific, Natick Mass.), Over-the-Wire Greenfield filter (Boston Scientific), TrapEase filter (Cordis Corp.) and the Günther Tulip filter (Cook Inc.)

Well-founded concerns over the long-term complications of permanent IVC filters, particularly in younger patients in need of PE prophylaxis with a temporary contraindication to anticoagulation, has led to the development of temporary and retrievable filters. Temporary filters remain attached to an accessible transcutaneous catheter or wire. These have been used primarily in Europe for PE prophylaxis during thrombolytic therapy for DVT. Currently these devices are not approved for use in the United States. Retrievable filters are very similar in appearance to permanent filters, but with modifications to the caval attachment sites and/or hooks at one end that can facilitate their removal. Retrievable filters that are currently available in the United States include the Günther Tulip (Cook Inc.), Opt Ease (Cordis Corp.), and Recovery nitinol filters (Bard Peripheral Vascular, Tempe, Ariz.) Lin P H, et al., Vena caval filters in the treatment of acute DVT. *Endovascular Today* 2005; January:40-50. The time limit of retrievability is in part dependant on the rate of endothelialization of the device, which typically occurs within 2 weeks. However, differences in design may extend the time period in which the filter may be safely retrieved.

Currently no consensus exists as to which patients have an indication for a retrievable filter. However, it is generally accepted that patients at high risk for pulmonary embolism or with documented PE and with a temporary contraindication to anticoagulation are candidates.

Certain circumstances preclude the placement of a filter in the infrarenal IVC. This includes thrombus extending into the infrarenal IVC, renal vein thrombosis or pregnancy. The safety of suprarenal placement of IVC filters is well documented, with no reported instances of renal dysfunction and no differences in the rates of filter migration, recurrent PE or caval thrombosis.

The rate of upper extremity DVT is on the rise. This is predominantly due to an increasing number of patients having short- and long-term upper extremity central venous access catheters. In one study, 88% of patients found to have an upper extremity DVT had a central venous catheter present at the site of thrombosis at the time of diagnosis or within the previous two weeks. Pulmonary embolism may complicate upper extremity DVT in 12-16% of cases. In patients who have such a complication or contraindication to anticoagulation, a filter can be safely placed immediately below the confluence of the brachiocephalic veins. However, misplacement of an SVC filter is theoretically more likely than with an IVC filter because of the relatively short target area for deployment.

The most common imaging modality used for filter insertion is fluoroscopy, performed either in an interventional suite or an operating room. Bedside placement of filters has inherent advantages, particularly for critically ill patients in intensive care settings where transport can be avoided. Portable fluoroscopy, surface duplex ultrasound and intravascular ultrasound (IVUS) have all been used to assist with bedside filter placement.

Vena cava filter placement frequently occurs concomitantly with central access line placement. Heretofore, however, there have been no devices which combine the function of a central access catheter and a removable vena cava filter.

SUMMARY OF THE INVENTION

The present invention relates to multi-lumen central access catheter having a vena cava filter at a distal end, a port proximal the filter and a port distal the filter and plural infusion ports. The proximal and distal ports permit measuring pressure and/or flow velocity across the filter as a determinant of extent of capture of embolic material in the filter or measuring flow rate at the position of the filter member as a positional indicator within the body. The proximal and distal ports also provide means for introducing a bioactive agent, such as an anticoagulant or thrombolytic agents, contrast medium, blood transfusions, fluids or medications. The multiple infusion ports also provide a means for introducing a flushing medium, such as saline, under elevated pressure to produce mechanical thrombolysis or induce thrombolysis by the infusion of thrombolytic agents directly to thrombus within the filter.

Accordingly, it is an objective of the present invention to provide a multi-lumen catheter coupled to a vena cava filter that is useful both as a central venous access catheter for administration of intravenous fluids, bioactive agents, contrast agents, flushing agents, pressurized fluids for mechanical thrombolysis and/or withdrawal of blood samples and for capture of thrombus or emboli.

Another aspect of the present invention is to provide a filter geometry in which the proximal portion of the filter, relative to the axis of blood flow, has larger interstitial openings to permit thrombus or embolic material to flow into the filter, while the distal portion of the filter, again relative to the axis of blood flow, has relatively smaller interstitial openings that capture the thrombus or embolic material within the filter. Another way to view this aspect is that the structure of the filter includes a greater open surface area exposed to the flow of embolic material into the filter at its proximal end, while the distal end has smaller open surface area exposed to the flow of embolic material to capture the embolic material in the distal end of the filter member.

DETAILED DESCRIPTION OF THE PREFERRED EMBODIMENTS

Turning to the accompanying Figures, in which like structural or functional elements are designated by like reference numerals, and with particular reference to FIGS. 1-5, according to a first embodiment of the invention, there is disclosed a central venous access filter ("CVAF") 10 that is composed generally of a multi-lumen central venous access catheter body 12 having a proximal port 32 associated with a first lumen 44 and a distal port 34 associated with a second lumen 42, a filter member 16, having a fixed proximal end 18 and a moveable distal end 20, is positioned generally intermediate the distal port 34 and the proximal port 32 and is generally concentric relative to the catheter body 12. An introducer sheath 22 is provided and provides a conduit for introducing the catheter body 12 and the filter member 16 in an unexpanded diametric state for delivery to a situs in the body. Prior to inserting the catheter and filter into the introducer sheath 22, the filter member 16 is constrained by a removable constraint (not shown), such as a sheath.

The multi-lumen aspect of the inventive central venous access filter catheter 10 is shown more clearly in FIGS. 2-5. The catheter body 12 has a proximal section 13 and distal section 14 which has a relatively smaller diametric profile than the proximal section 13. As described above, the first lumen 44 terminates at the proximal port 32, while the second lumen 42 terminates at the distal port 34. A central guidewire lumen 30 may be provided that extends the entire longitudinal length of the catheter body 12 and terminates at the distal end of the catheter body 12 at a distal guidewire opening 31 that permits the catheter body to track along a guidewire during a procedure. The central guidewire lumen 30 may also be used to introduce fluids, such as bioactive agents, intravenous fluids or blood transfusions.

Additionally, at least one of a plurality of infusion lumens 40 are provided, each having at least one infusion port 36 that passes through a wall of the catheter body 12. Bioactive agents, flushing fluids for flushing or under elevated pressures for mechanical thrombolysis of thrombus in the filter member 16, contrast agents or other fluids may be infused through the infusion lumens 40 and out of the at least one infusion port 36 to pass into the patient's venous system for either local or systemic effect. In accordance with one embodiment of the invention, plural infusion ports 36 are provided with multiple ports 36 being provided in communication with a single infusion lumen 40 and spaced along a longitudinal axis of the catheter body 12. Additionally, plural infusion ports 36 may be provided in a circumferentially spaced manner to provide for fluid infusion at points spaced around the circumference of the catheter body 12. In this manner, fluid infusion is provided along both the longitudinal axis and the circumferential axis of the catheter body 12 within the spatial area defined by and bounded by the filter member 16. Because the plural infusion ports 36 communicate with the spatial area defined by and bounded by filter member 16, fluids introduced through the infusion lumens 40 are directed immediately at thrombus caught within the filter member 16. This permits thrombolytic agents or high pressure mechanical thrombolysis using a pressurized saline flush to be introduced directly to the situs of thrombus capture within filter member 16.

In accordance with one embodiment of the invention, the preferred size of the introducer sheath 22 is an 8 Fr outer diameter (2.7 mm) while the preferred size of the catheter is a 6 Fr outer diameter (2.0 mm) with a diametric transition 15 between the proximal portion 13 and the distal portion 14 of the catheter body 12 corresponding to the thickness of the filter member 16. In this manner, the outer surface of the filter member 16 is substantially co-planar with the outer diameter of the proximal portion 13 of the catheter body 12 about its entire circumference. Moreover, the fixed proximal end 18 of filter 16 is positioned adjacent and in abutting relationship with the diametric transition 15, while the moveable distal end 20 of filter member 16 is concentrically positioned around the distal section 14 of catheter body 12 and is reciprocally moveable thereupon to accommodate diametric expansion of the filter member 16.

In order to aid a physician in visualizing the CVAF 10 in vivo, two radio-opaque markers are provided. A first radio-opaque marker 24 is provided at the distal end of the sheath 22 and a second radio-opaque marker 36 is provided at a distal tip 33 of the catheter body 12. It will be understood that when the sheath 22 is in its non-retracted delivery position, that the filter 16 will be covered and the first radio-opaque marker 24 and the second radio-opaque marker 36 will be adjacent or in close proximity with one another.

FIGS. 6-11 illustrate a second embodiment of the CVAF 50. Unlike CVAF 10, CVAF 50 does not include the central guidewire lumen 30 of CVAF 10. Rather, while the general construct of CVAF 50 is similar to that of CVAF 10, a different configuration of the inner lumens is employed.

CVAF 50, like CVAF 10, consists generally of a multi-lumen central venous access catheter body 12 having a proximal port 32 associated with a first lumen 54 and a distal port 34 associated with a second lumen 58, a filter member 16, having a fixed proximal end 18 and a moveable distal end 20, is positioned generally intermediate the distal port 34 and the proximal port 32 and is generally concentric relative to the catheter body 12.

The catheter body 12 has a proximal section 13 and distal section 14 which has a relatively smaller diametric profile than the proximal section 13. As described above, the first lumen 54 terminates at the proximal port 32, while the second lumen 58 terminates at the distal port 34. An atraumatic tip 52 terminates the catheter body 12 at its distal end. The atraumatic tip 52 preferably includes a radio-opaque marker to aid in positional visualization of the distal end of the catheter body 12.

A plurality of infusion lumens 56 are provided, each having at least one infusion port 36, preferably plural infusion ports 36, that passes through a wall of the catheter body 12 and communicates with a space defined within an area bounded by the filter member 16. Bioactive agents, flushing fluids, pressurized mechanical thrombolytic fluids, or other fluids may be infused through the infusion lumens 56 and out of the at least one infusion port 36 to pass into the space defined by the filter member 16 and ultimately into the patient's venous system for either local or systemic effect. In accordance with one embodiment of the invention, the each of the plural infusion lumens 56 are in fluid communication with plural ports 36 arrayed along both the longitudinal axis and the circumferential axis of the catheter body. This configuration provides for fluid infusion along both the longitudinal axis and the circumferential axis of the catheter body 12 and in direct communication with the space defined by the filter member 16 that captures thrombus.

The infusion lumens 56, the first lumen 54 and the second lumen 58 are bounded by and separated from each other by first catheter septum 51 and second catheter septum 56 which also aid in providing structural support for the catheter body 12. First catheter septum 51 is a generally diametrically and longitudinally extending member that divides the first lumen 54 from the second lumen 58 along the longitudinal axis of the catheter body 12. Second catheter septum 56 may comprise a generally U-shaped member that intersects the first catheter septum 51 at a lower aspect of the septum and is connected with an inner wall surface of the catheter body 12 at upper aspects of the septum 51 to define two infusion lumens in lateral regions of the catheter body 12.

Figure 1:
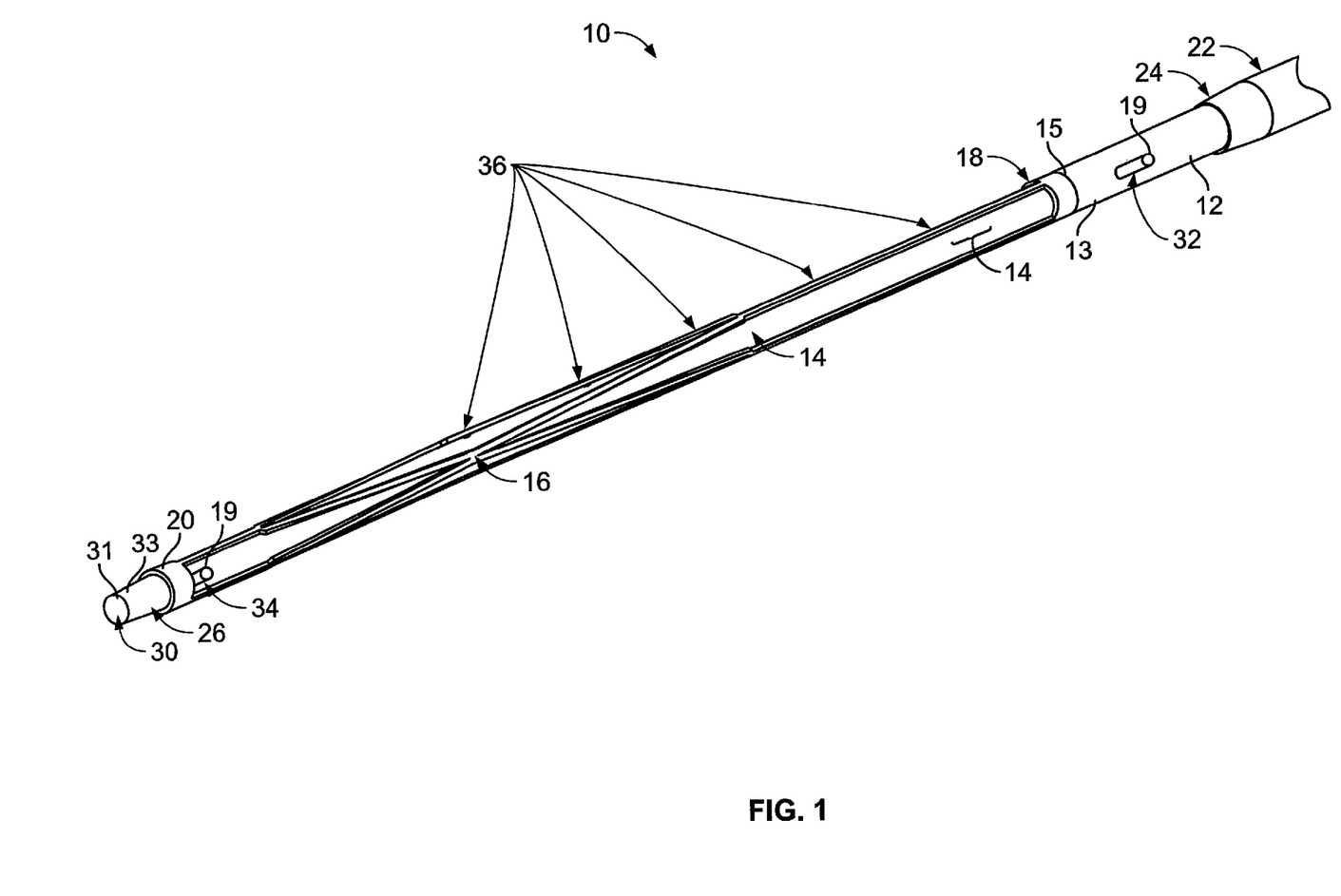
FIG. 1 is a perspective view of a central venous access vena cava filter catheter in accordance with a first embodiment of the present invention with the vena cava filter in an unexpanded state.
Figure 2:
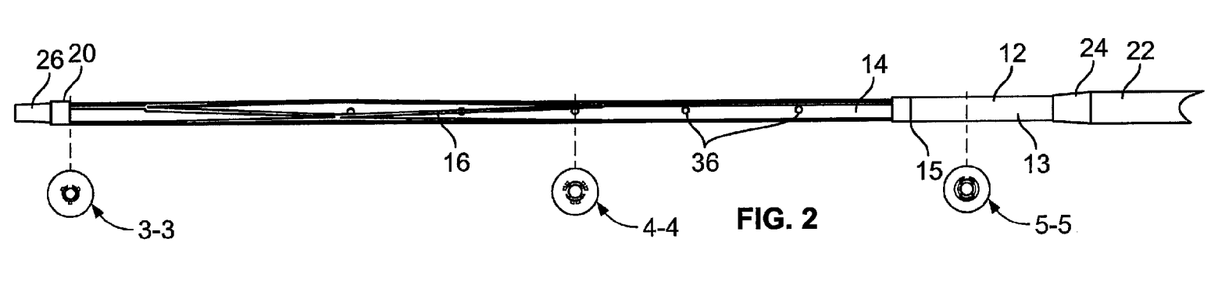
FIG. 2 is a side elevational view of a central venous access vena cava filter catheter in accordance with the first embodiment of the present invention.
Figure 3:
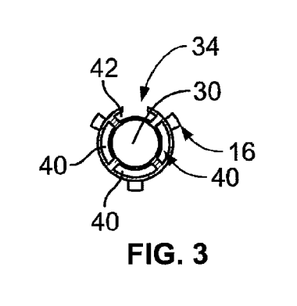
FIG. 3. is a cross-sectional view taken along line 3-3 of FIG. 2.
Figure 4:
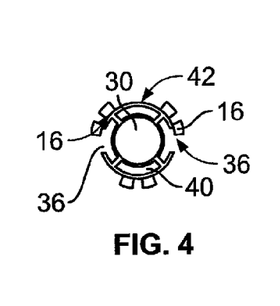
FIG. 4 is a cross-sectional view taken along line 4-4 of FIG. 2.
Figure 5:
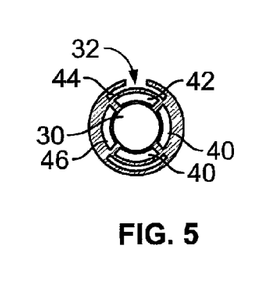
FIG. 5 is a cross-sectional view taken along line 5-5 of FIG. 2.
Figure 6:
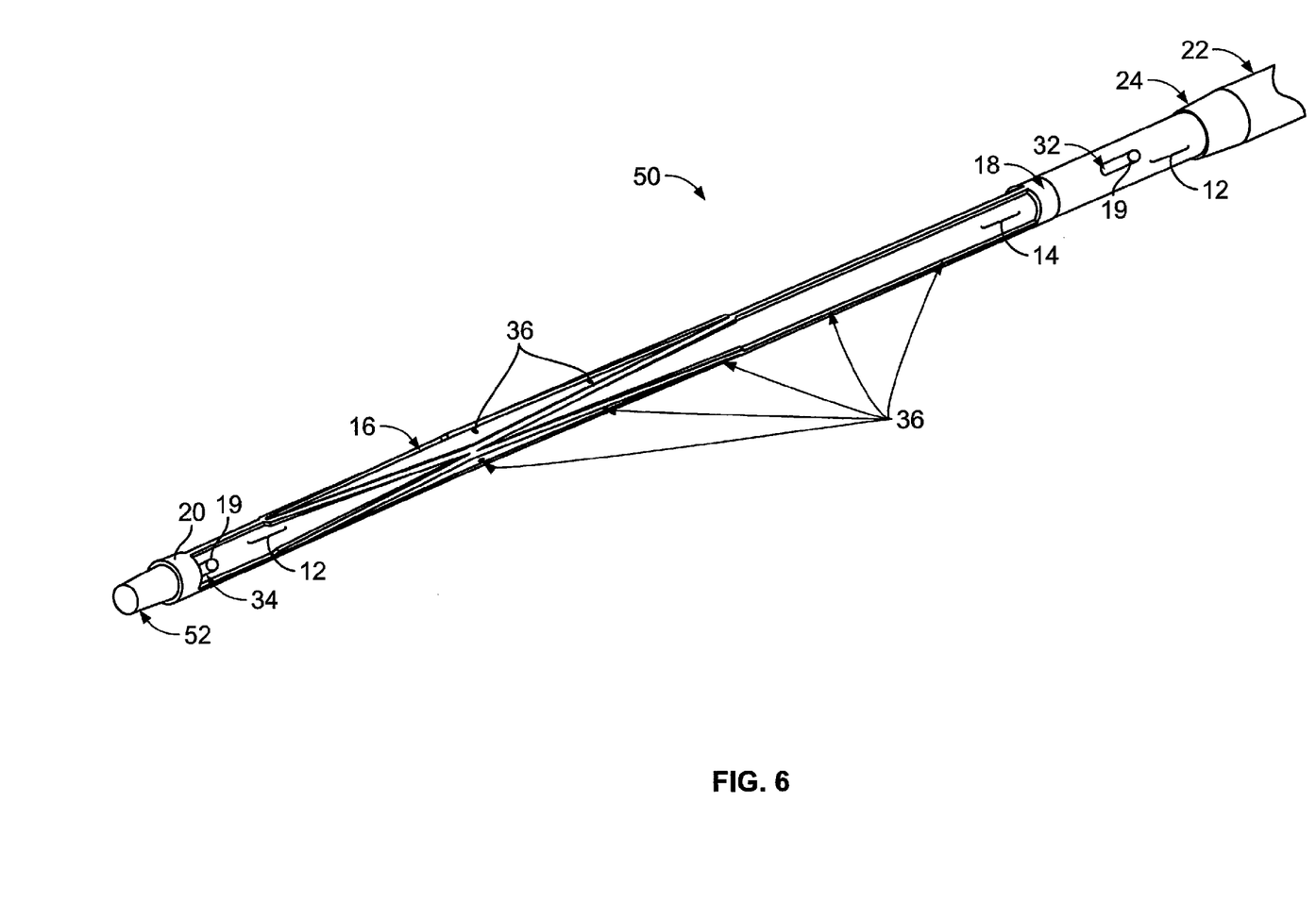
FIG. 6 is a perspective view of a central venous access vena cava filter catheter in accordance with a second embodiment of the present invention illustrating the vena cava filter in an unexpanded state.
Figure 7:
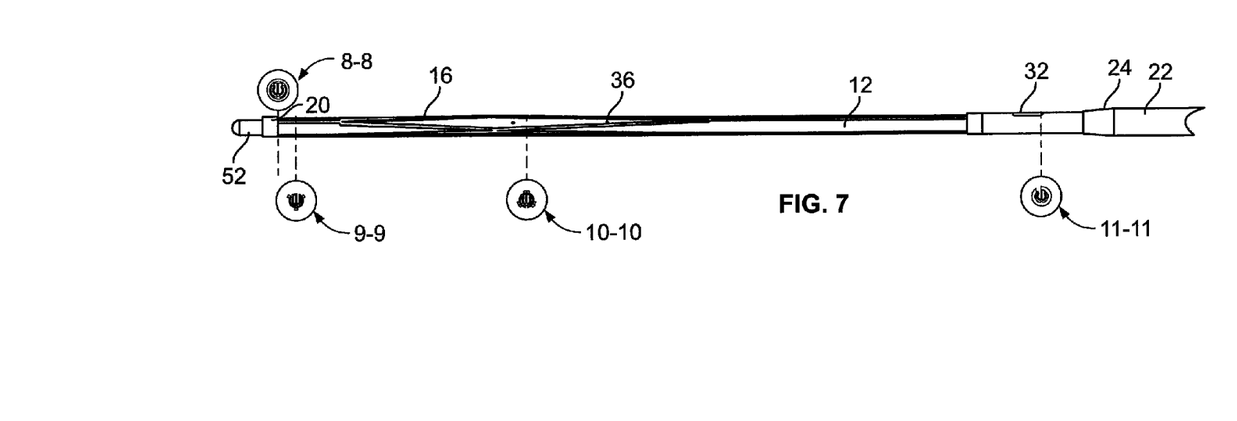
FIG. 7 is a side elevational view of a central venous access vena cava filter catheter in accordance with the second embodiment of the present invention.
Figure 8:
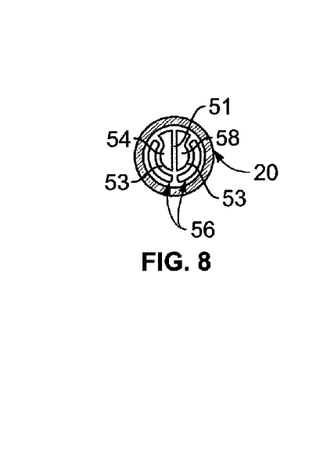
FIG. 8 is a cross-sectional view taken along line 8-8 of FIG. 7.
Figure 9:
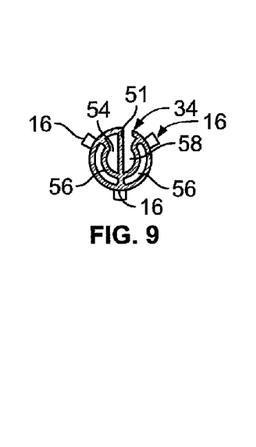
FIG. 9 is a cross-sectional view taken along line 9-9 of FIG. 7.
Figure 10:
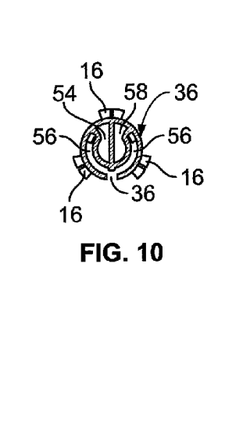
FIG. 10 is a cross-sectional view taken along line 10-10 of FIG. 7.
Figure 11:
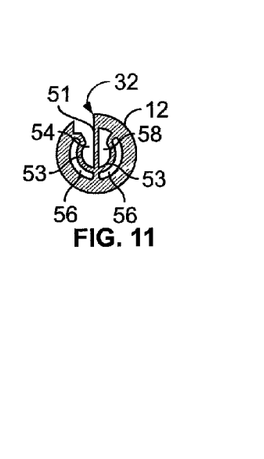
FIG. 11 is a cross-sectional view taken along line 11-11 of FIG. 7.
Figure 12:
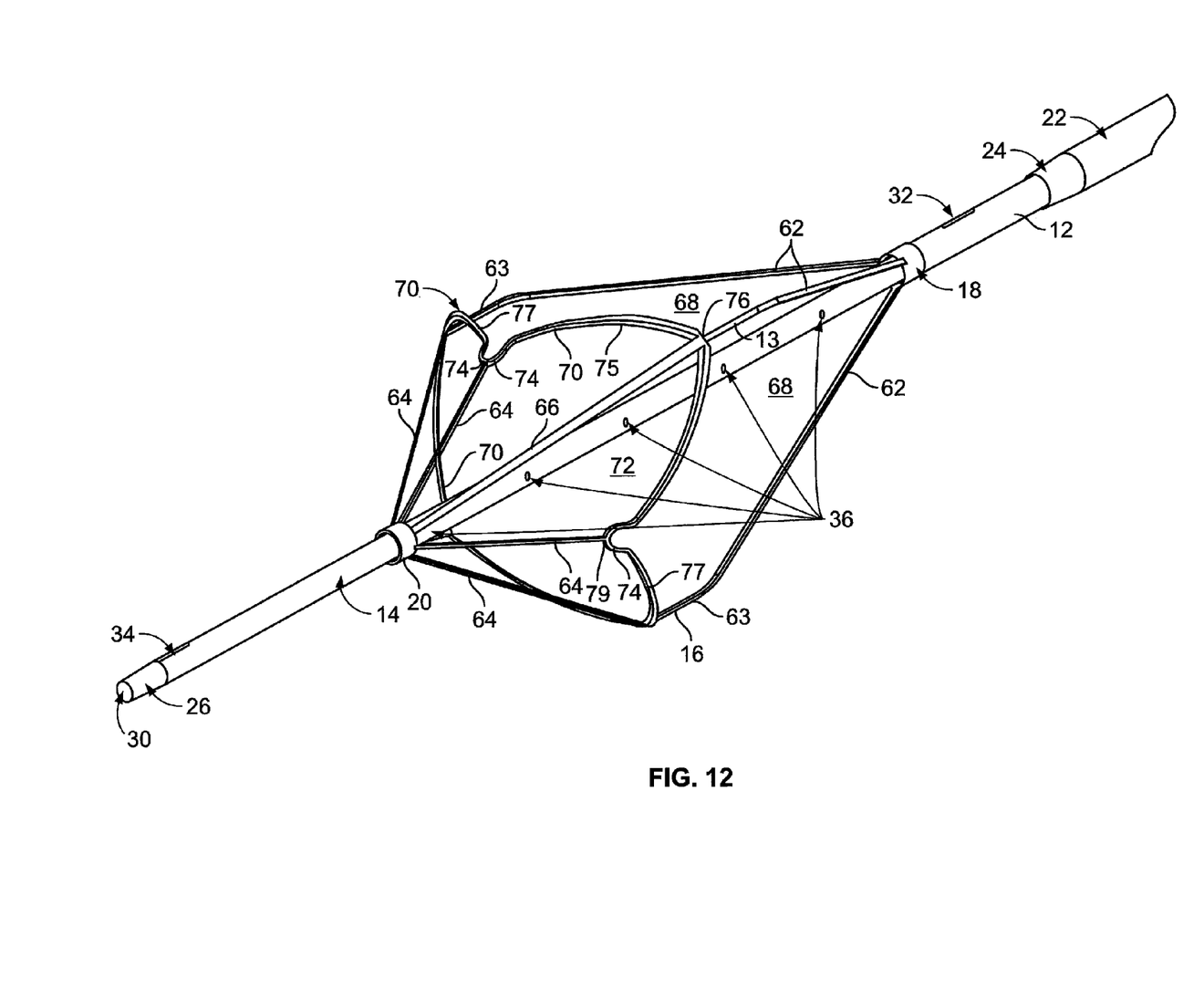
FIG. 12 is a perspective view of the central venous access vena cava filter catheter of FIG. 1 illustrating the vena cava filter in a diametrically expanded state.
Figures 13A, 13B, 13C, 13D:
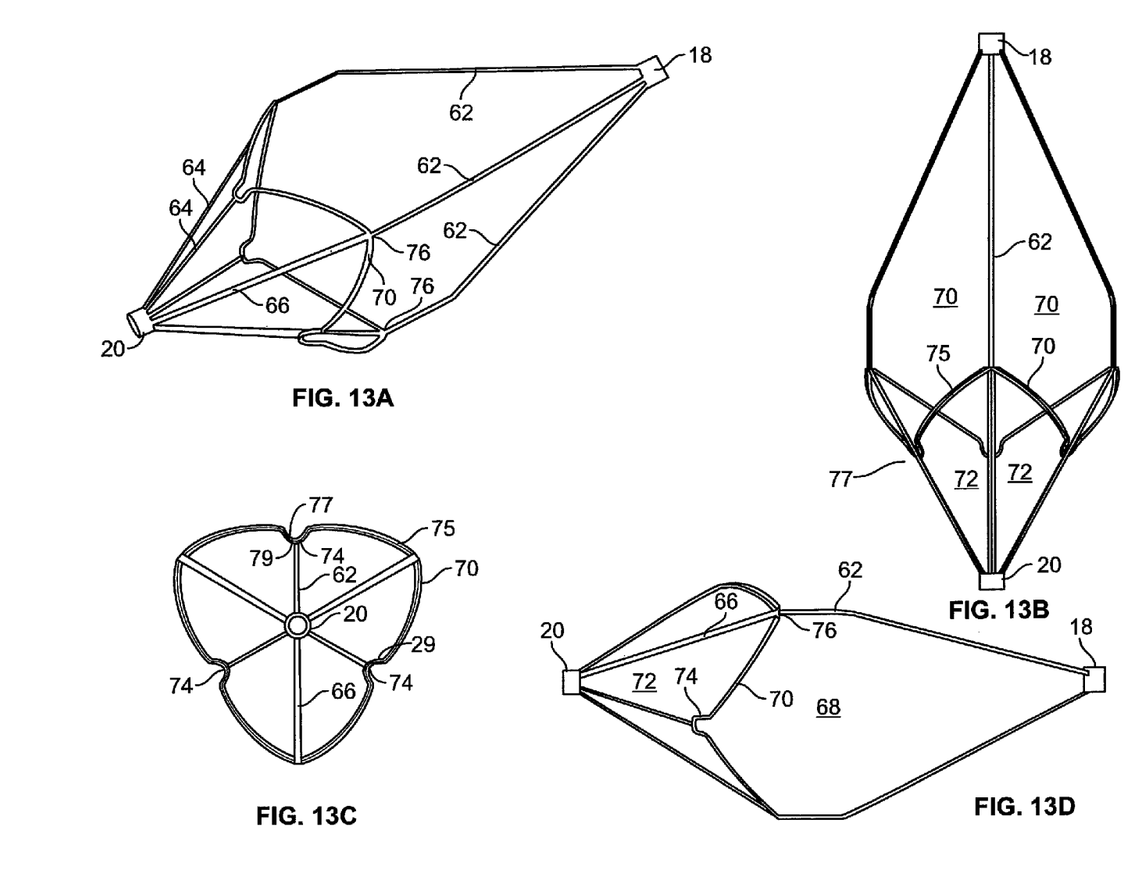
FIG. 13A is a perspective view of a vena cava filter member in accordance with a first embodiment thereof.
FIG. 13B is a first side elevational view thereof.
FIG. 13C is an end elevational view thereof.
FIG. 13D is a second side elevational view thereof.
Figures 14A, 14B, 14C, 14D:
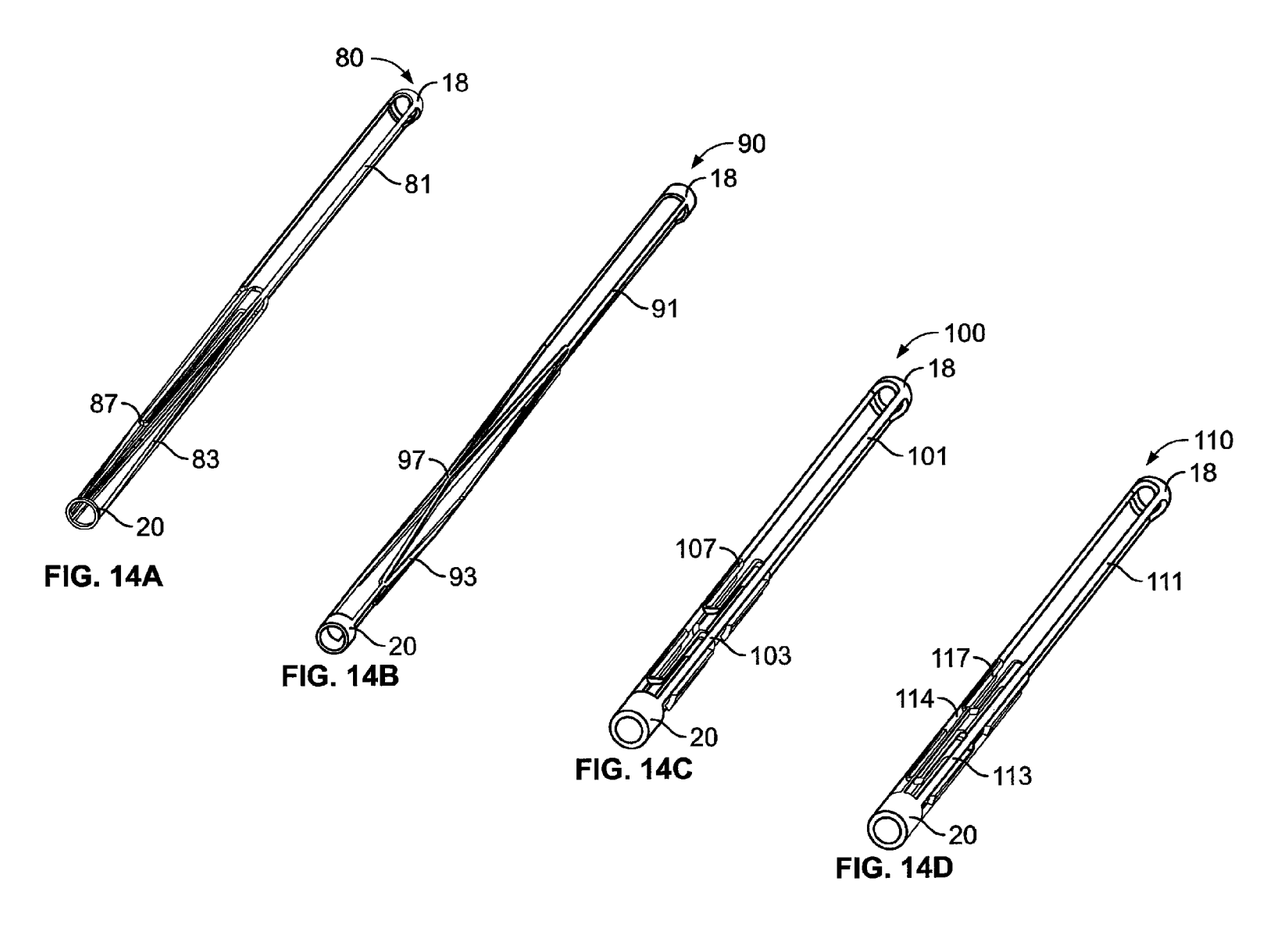
FIGS. 14A-14H are perspective views of alternative embodiments of a vena cava filter member in accordance with the present invention.
Figures 14E, 14F, 14G, 14H:
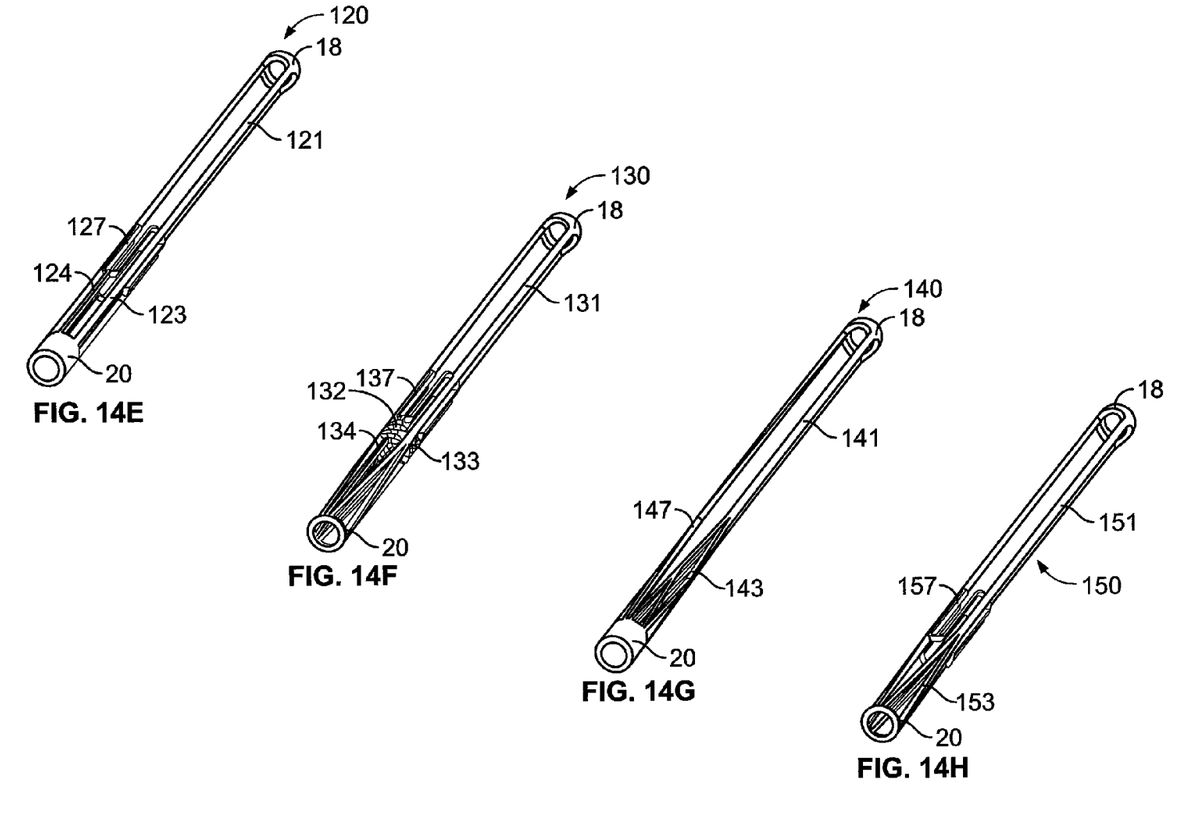
Figure 15A:
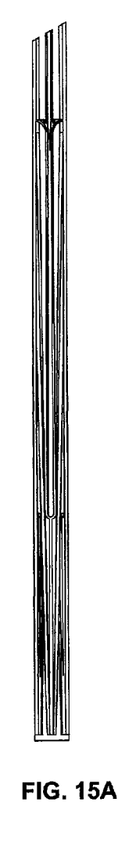
FIG. 15A-15H are fragmentary side elevational views of the alternative embodiments of the vena cava filter member illustrated in FIGS. 14A-14H.
Figure 15B:
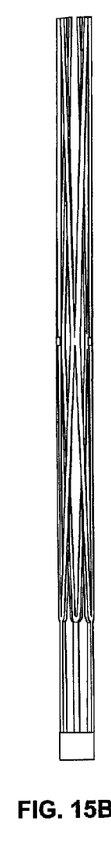
Figure 15C:
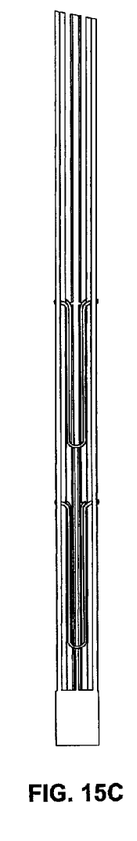
Figure 15D:
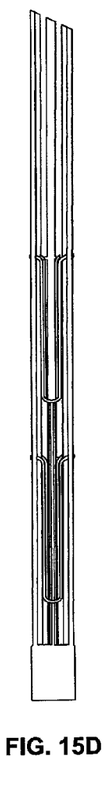
Figure 15E:
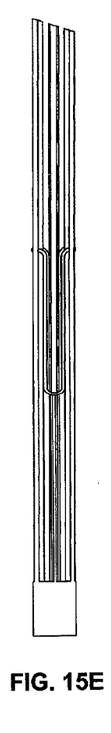
Figure 15F:
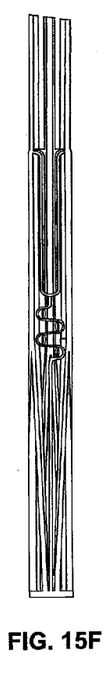
Figure 15G:
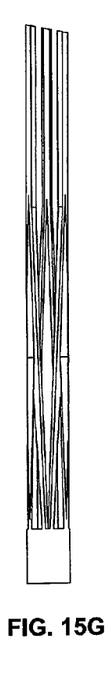
Figure 15H:
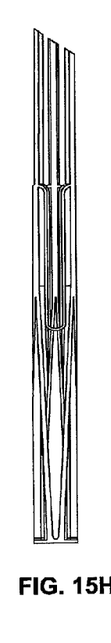

One embodiment of the filter member 16 is illustrated in its diametrically expanded configuration in FIGS. 12-13D. In this embodiment, filter member 16 consists generally of a proximal end 18 and a distal end 20, each of which consists generally of a tubular ring-like structure which is circumferentially positioned relative to the catheter body 12. A plurality of first strut members 62, preferably three, are coupled at their proximal end to the proximal end 18 of filter member 16 and each extends distally relative to the longitudinal axis of the catheter body 12. Each of the first strut members 62 is an elongate member that flares away from the central longitudinal axis of the catheter body 12 and terminates in a distal end section 63 that bends distally and is generally parallel with the longitudinal axis of the catheter body 12. A plurality of second strut members 64, preferably three, are coupled at their distal end to a the distal end 20 of filter member 16 and each extends proximally relative to the longitudinal axis of the catheter body 12. A plurality of third strut members 66, preferably three, are coupled at their distal ends to the distal end of the filter member and each extends proximally relative to the longitudinal axis of the catheter body 12. A hoop member 70 extends circumferentially to define a circumferential axis of the filter member 16 and has a series of continuous undulations defining peaks a series of peaks 77 and valleys 75 about the circumference of filter member 16. Each of the plurality of first strut members 62, the plurality of second strut members 64 and the plurality of third strut members 66 are coupled to the hoop member 70 at different points about its circumferential axis and intermediate the proximal end 18 and the distal end 20 of the filter member 16.

The plurality of first strut members 62 are preferably offset from each other by approximately 120 degrees about the circumference of the catheter body 12. The plurality of second strut members 64 are also preferably offset from each other by approximately 120 degrees. Finally, the plurality of third strut members 66 are also preferably offset from each other by approximately 120 degrees. Each of the plurality of first strut members 62 couple at a junction 76 to the hoop member 70 at a peak thereof. Similarly, each of the plurality of third strut members 66 couple at junction 76 to the hoop member 70 at a peak thereof. In this manner, a first strut member 62 and a third strut member 66 are each coupled to hoop member 70 at junction 76 and, in this relationship, form a generally linear member that extends along the longitudinal axis of the catheter body and connects between the proximal end 18 of the filter member 16 and the distal end 20 of the filter member 16. Each of the second strut members 64 couple, at their proximal ends to a valley 77 of the hoop member 70 and connects at a junction 79. Unlike the connections at junction 76 between the plurality of first strut members 62 and the plurality of second strut members, in this embodiment of the filter member 16, there is no member that connects to junction 79 and extends from the proximal end 18 of the filter member 16. In this configuration, the hoop member 70 assumes a generally circumferential tri-leaflet ring having three peaks 75 and three valleys 77.

To facilitate bending and folding of the hoop member 70 between the expanded and unexpanded states, generally U-shaped hinge members 74 may be provided at each of the valleys 77 of the hoop member 70. It will be understood that each of the plurality of first strut members 62, plurality of second strut members 64, plurality of third strut members 66 and the hoop member 70 are preferably fabricated of biocompatible materials, such as shape memory alloys, superelastic materials or elastic materials, including, without limitation, titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, cobalt-chromium-molybdenum alloys, nitinol, and stainless steel.

FIGS. 14A-14H and corresponding FIGS. 15A-15H depict alternative embodiments of the filter member 16, labeled 80, 90, 100, 110, 120, 130, 140 and 150, respectively. Like filter member 16, each of filter members 80, 90, 100, 110, 120, 130, 140 and 150 having a proximal end 18 and a distal end 20 that each consist of a generally ring-like structure intended to circumferentially couple to a catheter body 12 (not shown), with the proximal end 18 being fixed and the distal end 20 being reciprocally moveable axially along the distal portion 14 of catheter body 12. Like filter member 16, each of the alternative filter member embodiments depicted in FIGS. 14A-14H and 15A-15H, consist of a plurality of first strut members 81, 92, 101, 111, 121, 131, 141 and 151, respectively, extending distally from the proximal end 18 of the filter member and a plurality of second strut members 83, 93, 103, 113, 123, 133, 143 and 153, respectively, extending proximally from the distal end 20 of the filter member, with a diametrically expansible hoop member 87, 97, 107, 117, 127, 137, 147, 157, respectively, interconnecting the distally extending strut members 81, 92, 101, 111, 121, 131, 141 and 151, respectively, with the proximally extending strut members 83, 93, 103, 113, 123, 133, 143 and 153. In the alternative embodiments of filter members 100, 110 and 120, at least some distally extending strut members and at least some of the proximally extending strut members form linear elements that extend along the entire longitudinal axis of the respective filter member, with the hoop member being comprised of at least one undulating or serpentine ring structure.

In the alternative embodiments of filter members 80, 90, 130, 140 and 150, a plurality of distally extending strut members are provided spaced approximately 120 degrees apart from one and other about the circumference of the filter members, and the distally extending strut members bifurcating once or twice distally in a generally Y-shaped manner as in filter members 80, 130, 140 or 150, or the proximally extending strut members bifurcating proximally in a generally Y-shaped manner and interconnecting with the distally extending generally Y-shaped strut members to form a diamond-like pattern as in filter member 90. In filter members 90 and 140, the hoop member is formed by the diamond-like pattern formed by the intersection of the plurality of struts. In contrast, in filter members 80, 130 and 150, the hoop member is formed by at least one undulating or serpentine ring structure which is diametrically expansible. As illustrated in filter members 110, 120 and 130, apical portions of each undulating or serpentine ring structure is interconnected by an interconnecting member 114, 124, 134, respectively, either with an adjacent ring structure, as in filter member 110 or to a distal end 20 of the filter member itself. A longitudinally serpentine section 132 in filter 32 may be provided in conjunction with the interconnecting member 134, to afford greater expansive properties to the hoop member 137.

Each of the foregoing embodiments of the filter member are characterized by a filter having a greater open surface area exposed to the flow of embolic material into the filter at its proximal end, while the distal end has smaller open surface area exposed to the flow of embolic material to capture the embolic material in the distal end of the filter member. Additionally, each of the foregoing embodiments of the filter member are self-centering to provide proper apposition and centering with a blood vessel and maximize the flow dynamics of the filter member within the blood vessel for purposes of capturing embolic material within the struts of the filter.

As noted above, the proximal 32 and distal 34 ports serve as means for measuring flow rates or pressure differentials across the filter 16. This may be accomplished by including flow sensors and/or pressure transducers 19 in operable association with each port 32, 34, with the associated electrical connections to the flow sensors an/or pressure transducers 19 passing through the respective lumens associated with each port 32, 34 and terminating at the proximal end of the catheter body 12. Where flow sensors 19 are employed, a single flow sensor associated with proximal port 32, the distal port 34 or the distal end of sheath 22 may be sufficient to detect fluid flow rate at the position of the catheter body 12. By providing a flow sensor at the distal end of sheath 22, the clinician will be able to determine flow velocity at the distal end of the introducer sheath 22 prior to introducing the catheter body 12 and make fine adjustments to the placement of the distal end of the introducer sheath 22 to ensure proper placement for the filter member 16. Plural flow sensors 19 may be employed and operably associated with each of proximal port 32 and distal port 34 to sense changes in flow velocity across the filter member 16. Alternatively, the flow sensors and/or pressure transducers 19 may reside in communication with the lumens respectively associated with each port 32, 34 at the proximal end of the catheter body 12, thereby eliminating the need for electrical connectors resident with the associated lumens. Furthermore, wireless flow sensors and/or pressure transducers may be provided in communication with each port 32, 34, and be operably coupled to a power source and a transmitter to wirelessly transmit telemetry data from the transducers to a wireless receiver in communication with the transmitter, as is known in the art.

It is known that flow rate increases proximally within the venous system. For example a flow rate of 1 L/min is typical in one femoral vein, increases to 2 L/min in the inferior vena cava and increasing another 0.7 to 1 L/min proximate the renal veins. Knowing the typical flow velocities in vessels of different transverse cross-sectional areas, coupled with a flow sensor 19 associated with the multi-lumen catheter body 12 may serve to supplement or replace the requirements for fluoroscopy or sonography in placement of the CVAF 10, 50.

Other sensors, such as, for example, chemosensors, color sensors, electrical sensors or biosensors, may be employed in lieu of or in addition to pressure transducer and/or a flow sensor 19 in order to detect other changes or conditions within the patient's vasculature. For example, color sensors exist that sense color changes in thrombus, such color changes may be displayed and interpreted by the medical practitioner as an indication of thrombus staging. Analyte sensors, such a as a glucose sensor or an oxygen saturation sensor may also be employed.

The filter member 16, or its alternative embodiments described above, may be fixed to the catheter body 12 or may be removably coupled to the catheter body 12 for deployment as a temporary and retrievable vena cava filter. Removable coupling of the filter member to the catheter body 12 may be accomplished with a variety of release and retrieval mechanisms operably associated the catheter body 12 and proximate the diametric transition 15. Non-limiting examples of such release and retrieval mechanisms include a wire release that engages with a the proximal end 18 of the filter, a cooperating indexed detent and projection interaction between the catheter body 12 and the proximal end 18 of the filter, such as a detent in the proximal end of the filter and a cooperating projection in the multi-lumen catheter that is positionally indexed to the detent and releasable from the detent, or, alternatively, a helical slot or threads may be formed in the proximal end 18 of the filter and indexed and cooperating projection in the multi-lumen catheter than permits engagement and disengagement with the helical slot or threads.

In use, the introducer sheath 22 is first placed into the body in a normal manner for introducing a central venous line. Specifically, after accessing a vein using a large bore needle, under local anesthesia, a guidewire is inserted through the needle bore and passed into the vein. Once the guidewire is positioned, the needle is withdrawn, and a dilator together with the introducer sheath 22 introduced over the guidewire. Once the introducer sheath 22 is positioned at a desired location within the venous system under radiography, the dilator may be removed from the patient. The first radio-opaque marker 24 assists in positional visualization of the distal end of the introducer sheath 22. The constraining sheath covering the filter 16 is removed while introducing the filter member 16 and catheter body 12 into the introducer sheath 22, which constrains the filter member 16 during its passage through the introducer sheath 22. Once the distal end of the catheter body 12 reaches the distal end of the introducer sheath 22, the filter is deployed. If the filter therapy alone is desired, the filter member 16 is detached from the catheter body 12 and the catheter body 12, introducer sheath 22 and guidewire is withdrawn from the patient. Where both central venous access and filter therapy is desired, the introducer sheath 22 and catheter body 12 with the filter member 16 is left in the patient until withdrawal is required.

Retrieval and removal of a detached filter member 16 is accomplished using a second procedure under local anesthesia which substantially replicates the placement of the CVAF, with a capture sheath (not shown), similar to introducer sheath 22, being introduced, a retrieval catheter being introduced through the sheath, and engaging the filter member 16, then withdrawn into the capture sheath to collapse the filter member 16, with the entire assembly of the filter member 16, catheter body 12, capture sheath and guidewire, if used, is withdrawn from the patient.

Thus there has been described a central venous access filter in accordance with the foregoing embodiments of the invention which include, generally, a multi-lumen catheter body, a filter member and an introducer sheath. The multi-lumen catheter body has a plurality of ports each of which are in fluid flow communication with at least one lumen in the multi-lumen catheter body. Lumens may include a central guidewire lumen useful for tracking over a guidewire and/or larger volume infusion of bioactive agents, intravenous fluids, blood transfusions, or other fluids; infusion lumens in communication with infusion ports positioned to direct fluids to the space bounded by the filter member for introducing bioactive agents, including thrombolytic agents or flushing agents, including pressurized fluids for mechanical thrombolysis directly to the capture site of the thrombus in the filter member; and lumens communicating with proximal and distal ports which may also be used for fluid introduction and/or may house or communicate with sensors, such as pressure transducers, flow sensors, analyte sensors, color sensors, or the like. The filter member may be detachable from the multi-lumen catheter body to permit temporary filter placement and later retrieval by a detachment mechanism that cooperates between the filter and the multi-lumen catheter body. These and other aspects of the present invention are provided by way of non-limiting examples, with the claims appended hereto serving to define the scope of the subject matter regarded as the invention.

What is claimed is:

1. A multi-lumen vena cava filter catheter, comprising:
a generally cylindrical catheter member having a generally cylindrical outer wall surface, a first lumen passing longitudinally through the generally cylindrical catheter member and at least a second lumen passing longitudinally through the generally cylindrical catheter member and spaced from the first lumen, the first lumen and second lumen being separated by a portion of the generally cylindrical catheter member, wherein the second lumen is operable as a guidewire lumen;
a first opening in the generally cylindrical outer wall communicating with the first lumen and a second opening communicating with the second lumen; and
a vena cava filter member circumferentially coupled about a distal end of the catheter member and having a first end coupled circumferentially in fixed relation to the catheter member and a second end circumferentially and moveably coupled to the catheter member, the vena cava filter member consisting of a first plurality of struts configured to form a generally frustroconical proximal section of the vena cava filter member tapering proximally and having proximal interstitial openings, and a second plurality of struts configured to form a generally frustroconical distal section of the vena cava filter member tapering distally and having distal interstitial openings, the frustroconical proximal section having a length that is greater than or less than a length of the frustroconical distal section, each of the proximal interstitial openings having an open surface area either greater than or less than the open surface area of each of the distal interstitial openings, and a third plurality of struts forming a hoop portion coupling a distal end of the first plurality of struts to a proximal portion of the second plurality of struts; the vena cava filter member being positioned generally intermediate the first opening and second opening and configured to be expanded in a patient's blood vessel such that a transverse dimension of the filter decreases in the direction of the patient's blood flow to collect thrombi, wherein the vena cava filter member centers the catheter member within a blood vessel lumen.

2. The multi-lumen vena cava filter catheter according to claim 1, further comprising a sheath member concentrically disposed over the generally cylindrical catheter member and the vena cava filter member and coaxially movable relative to the generally cylindrical catheter member and vena cava filter member to deploy and collapse the vena cava filter member.

3. The multi-lumen vena cava filter catheter according to claim 2, further comprising an annular space between the generally cylindrical outer wall surface of the generally cylindrical catheter member and an inner wall surface of the sheath, wherein the annular space terminates at an annular opening at a distal end of the sheath.

4. The multi-lumen vena cava filter catheter according to claim 3 further comprising, in combination, a thrombolytic agent introducible through at least one of the first lumen, the second lumen or the annular space.

5. The multi-lumen vena cava filter catheter according to claim 1, further comprising a pressure transducer operably associated with the at least one of the first opening and the second openings.

6. The multi-lumen vena cava filter catheter according to claim 1, further comprising a sensor operably associated with at least one of the first opening and the second opening, wherein the sensor detects a condition within a patient's body near the multi-lumen vena cava filter catheter.

7. The multi-lumen vena cava filter catheter according to claim 1, further comprising a flow sensor operably associated with at least one of the first and second openings.

8. The multi-lumen vena cava filter catheter according to claim 1, further comprising a third lumen disposed longitudinally through the generally cylindrical catheter member, and wherein at least one infusion port is associated with the third lumen and positioned within an area of the multi-lumen catheter body bounded by the filter member.

9. The multi-lumen vena cava filter catheter according to claim 8, wherein the at least one infusion port further comprises a plurality of infusion ports arrayed along a longitudinal axis and a circumferential axis of the multi-lumen catheter body and within the area bounded by the filter member.

10. The multi-lumen vena cava filter catheter according to claim 8, further comprising, in combination, a thrombolytic agent introducible through the third lumen.

11. The multi-lumen vena cava filter catheter according to claim 1, wherein the hoop portion further comprises a generally sinusoidal-shaped member having a plurality of peaks and valleys.

12. The multi-lumen vena cava filter catheter according to claim 11, wherein each of the first plurality of struts and each of the second plurality of struts is connected to one of the plurality of peaks and valleys of the generally sinusoidal-shaped member.

13. The multi-lumen vena cava filter catheter according to claim 12, wherein at least one of the plurality of peaks and valleys of the generally sinusoidal shaped member further comprises a generally U-shaped hinge member and one of the first plurality of struts or one of the second plurality of struts is coupled to an apex of the generally U-shaped hinge member.

14. A multi-lumen vena cava filter catheter, comprising:
a generally cylindrical catheter member having a generally cylindrical outer wall surface, a first lumen passing longitudinally through the generally cylindrical catheter member and at least a second lumen passing longitudinally through the generally cylindrical catheter member and spaced from the first lumen, the first lumen and second lumen being separated by a catheter septum extending diametrically and longitudinally through the center of the generally cylindrical catheter member between the first and second lumens;
a first opening in the generally cylindrical outer wall communicating with the first lumen and a second opening in the catheter member communicating with the second lumen; and
a vena cava filter member circumferentially coupled about a distal end of the central venous line catheter body and having a first end coupled circumferentially in fixed relation to the cylindrical catheter member and a second end circumferentially moveably coupled to the cylindrical catheter member,
the vena cava filter member consisting of a plurality of struts configured to form a generally frustroconical proximal section of the vena cava filter member tapering proximally and having proximal interstitial openings, and a generally frustroconical distal section of the vena cava filter member tapering distally and having distal interstitial openings, the frustroconical proximal section having a length that is greater than or less than a length of the frustroconical distal section, each of the proximal interstitial openings having an open surface area either greater than or less than the open surface area of each of the distal interstitial openings; the vena cava filter member being positioned generally intermediate the first opening and second opening and configured to be expanded in a patient's blood vessel such that a transverse dimension of the filter decreases in the direction of the patient's blood flow to collect thrombi, wherein the vena cava filter member centers the cylindrical catheter member within a blood vessel lumen.

15. The multi-lumen vena cava filter catheter according to claim 14, further comprising a sheath member concentrically disposed over the generally cylindrical catheter member and the vena cava filter member and coaxially movable relative to the generally cylindrical catheter member and vena cava filter member to deploy and collapse the vena cava filter member.

16. The multi-lumen vena cava filter catheter according to claim 15, further comprising an annular space between the generally cylindrical outer wall surface of the generally cylindrical catheter member and an inner wall surface of the sheath, wherein the annular space terminates at an annular opening at a distal end of the sheath.

17. The multi-lumen vena cava filter catheter according to claim 16, further comprising, in combination, a thrombolytic agent introducible through at least one of the first lumen, the second lumen or the annular space.

18. The multi-lumen vena cava filter catheter according to claim 14, further comprising a pressure transducer operably associated with the at least one of the first opening and the second opening.

19. The multi-lumen vena cava filter catheter according to claim 14, further comprising a sensor operably associated with at least one of the first opening and the second opening, wherein the sensor detects a condition within a patient's body near the multi-lumen vena cava filter catheter.

20. The multi-lumen vena cava filter catheter according to claim 14, further comprising a flow sensor operably associated with at least one of the first and second openings.

21. The multi-lumen vena cava filter catheter according to claim 14, further comprising at least one infusion lumen disposed longitudinally through the generally cylindrical catheter member, and wherein at least one infusion port is associated with each of the at least one infusion lumen and positioned within an area of the multi-lumen catheter body bounded by the filter member.

22. The multi-lumen vena cava filter catheter according to claim 21, wherein the at least one infusion port further comprises a plurality of infusion ports arrayed along a longitudinal axis and a circumferential axis of the multi-lumen catheter body and within the area bounded by the filter member.

23. The multi-lumen vena cava filter catheter according to claim 21, further comprising, in combination, a thrombolytic agent introducible through the at least one infusion lumen.

24. The multi-lumen vena cava filter catheter according to claim 14, wherein the plurality of struts further include a first set of struts affixed at a proximal end to the proximal portion of the filter member, a second set of struts affixed at a distal end thereof to the distal portion of the filter member, and a third set of struts forming a hoop portion coupling a distal end of the first set of struts to a proximal portion of the second set of struts.

25. The multi-lumen vena cava filter catheter according to claim 24, wherein the hoop portion further comprises a generally sinusoidal-shaped member having a plurality of peaks and valleys.

26. The multi-lumen vena cava filter catheter according to claim 24, wherein each one of the plurality of struts is connected to one of the plurality of peaks and valleys of the generally sinusoidal-shaped member.

\* \* \* \* \*